Sept. 24, 1974 G. Y. NAKANO Plant Pat. 3,624
CHRYSANTHEMUM PLANT ENTITLED DARK PINNACLE
Filed Aug. 30, 1973
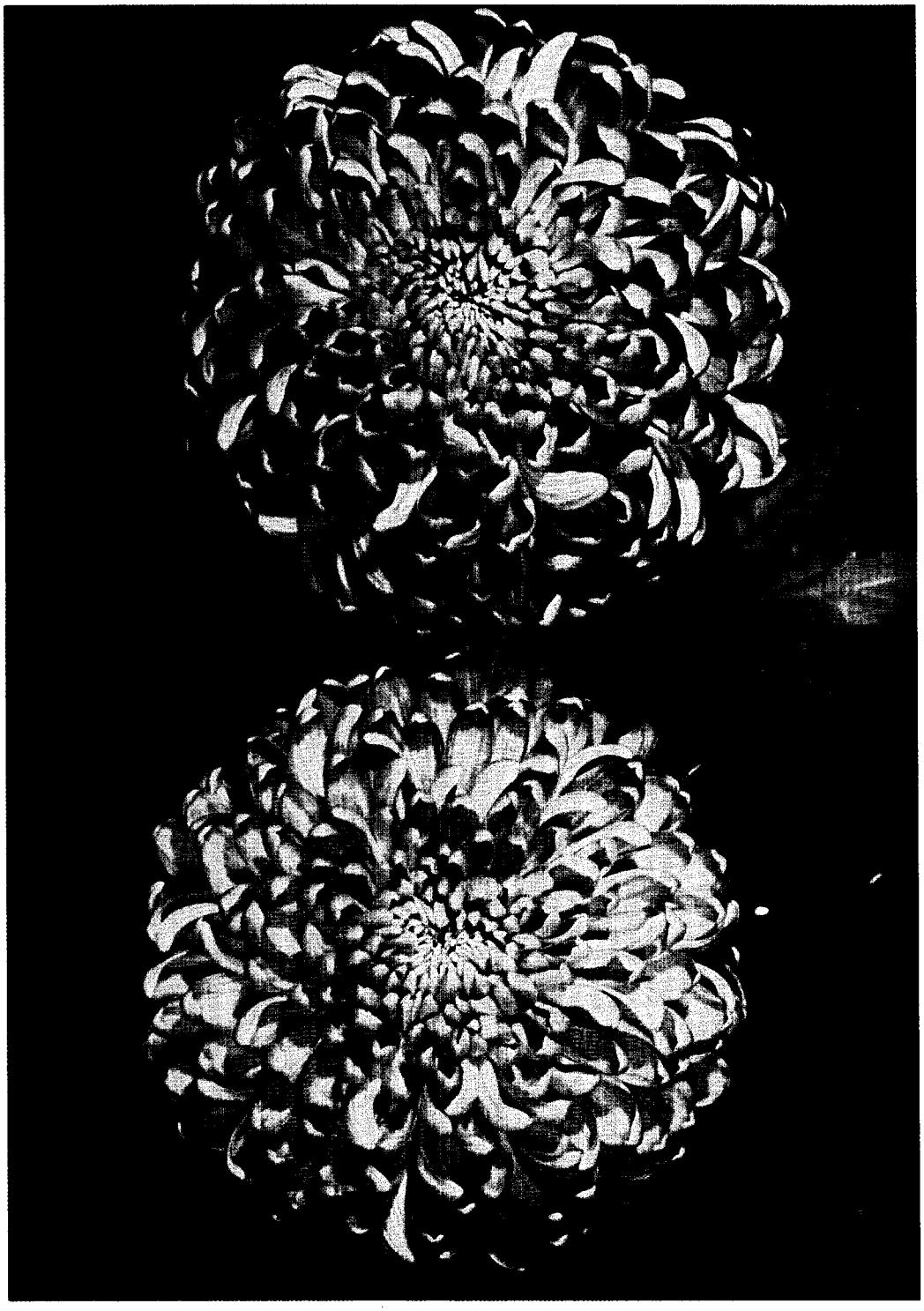

United States Patent Office

Plant Pat. 3,624
Patented Sept. 24, 1974

3,624

CHRYSANTHEMUM PLANT ENTITLED DARK PINNACLE

Grace Y. Nakano, 1166 Bryant Ave., Mountain View, Calif. 94040

Filed Aug. 30, 1973, Ser. No. 392,953
Int. Cl. A01h *5/00*
U.S. Cl. Plt.—81 1 Claim

This invention relates to a new and distinct variety of chrysanthemum plant which is a sport of Escapade, an unpatented but commercial variety.

This sport was selected from a flowering in my commercial greenhouses in Mountain View, Calif., because of its improved dark color, as compared to Escapade. The plant was revegetated and through repeated flowerings the growth proved to be three to five inches shorter than Escapade with a response bloom time of three to five days earlier. At the time of maturity, when the first flowers were cut it was possible to cut fifty percent of the darker sport as opposed to only five percent of the Escapade, which results in all of the dark sport being cut three to five days with twenty-five percent of the Escapade still remaining.

This new sport is similar to Escapade in the following characteristics:

1. Foliage shape
2. Size of Flower
3. Heavy stem and growth

Asexual reproduction of my new and distinct variety has proven to be consistent in:

1. Vegetative growth
2. Claims of flower characteristics

The overall growth characteristics may vary according to environmental conditions under which it is grown, however, here in the Bay Area of California it has a response period of approximately 7½ weeks and is suggested for year round production.

The accompanying drawing illustrates the color as being as true as possible with color illustrations of this type. The upper flower shows the new variety whereas the lower flower shows a comparison of the new variety on the top with Escapade on the bottom. The color of the new variety will be apparent in the photograph.

The color designation is by use of the Royal Horticulture Society color chart, R. F. Wilson, of the Royal Horticulture Society of London, England.

Plant:

*Botanical classification.*—*Chrysanthemum morifolium* Ramat.

*Origin.*—Selected from commercial flowering.

*Form.*—Herbaceous.

*Height.*—36–40".

*Growth.*—Strong vigorous; upright.

| | Dark Pinnacle | Escapade | Promenade |
|---|---|---|---|
| Leaf: | | | |
| Size | 16.2 cm. x 10 cm. (avg.) | 16.2 cm. x 10 cm. (avg.) | 16.2 cm. x 10 cm. (avg.). |
| Shape | Ovate, deeply lobed | Ovate, deeply lobed | Ovate, deeply lobed. |
| Texture | Smooth, finely pubescent | Smooth, finely pubescent | Smooth, finely pubescent |
| Ribs and veins | Prominent | Prominent | Prominent. |
| Margin | Deeply lobed | Deeply lobed | Deeply lobed. |
| Color | Yellow green 147/A | Yellow green 147/A | Green 139/A. |
| Bud: | | | |
| Diameter | 3.4 cm | 3.5 cm | 3.2 cm. |
| Depth | 2.5 cm | 2.3 cm | 2.3 cm. |
| Color | Red purple 74/D | Red purple 65/C | Red purple 65/C: |
| Flower color: | | | |
| Center of flower | Red purple 73/D | Red purple 65/D | Red purple 65/D. |
| Base of petal (¼" from end) | Red purple 74/D | Red purple 73/C | Red purple 68/C. |
| Inside of petal | Red purple 74/B | Red purple 74/D | Red purple 74/D. |
| Reverse of petal | Purple 75/C | Purple 75/C | Purple 75/C. |
| Tonality from distance | Red purple 74/C | Red purple 65/B | Red purple 73/B. |
| Other characteristics: | | | |
| Size of flower | 13.5 cm. x 8.84 cm | 13.4 cm. x 8.95 cm | 13.5 cm. x 6.25 cm. |
| Stamens | Numerous | Few | None. |
| Pollen | None visible | None visible | Do. |
| Pistil | Present | Present | Present. |

This new selection is different from Escapade in the following ways:

1. Intense and darker color
2. Three to five inches shorter plant growth
3. Less bruising
4. Resistance to fading
5. Three to five days earlier flower response
6. Lower percentage of culls

I claim:

A new and distinct variety of chrysanthemum having the characteristics of a darker flower, three to five days earlier flower response; three to five inches shorter mature growth; and numerous stamens present, which characteristics show a distinct difference over Escapade and Promenade.

No references cited.

ROBERT E. BAGWILL, Primary Examiner

UNITED STATES PATENT OFFICE
CERTIFICATE OF CORRECTION

Patent No. Plant Patent 3,624 Dated September 24, 1974

Inventor(s) Grace Y. Nakano

It is certified that error appears in the above-identified patent and that said Letters Patent are hereby corrected as shown below:

Column 1, line 23, after "cut" insert ---after---

Signed and sealed this 14th day of January 1975.

(SEAL)
Attest:

McCOY M. GIBSON JR.
Attesting Officer

C. MARSHALL DANN
Commissioner of Patents